United States Patent [19]

Heinix

[11] Patent Number: 4,642,050
[45] Date of Patent: Feb. 10, 1987

[54] ALIGNMENT CAP FOR MOUNTING ARTIFICIAL TEETH ON WORKING MODELS

[75] Inventor: Lucien J. Heinix, Antwerp, Belgium
[73] Assignee: Alphadent, Belgium
[21] Appl. No.: 720,178
[22] Filed: Apr. 5, 1985
[30] Foreign Application Priority Data Apr. 20, 1984 [BE] Belgium ............................ 2/60396

[51] Int. Cl.⁴ .......................................... A61C 11/00
[52] U.S. Cl. .................................................. 433/56
[58] Field of Search .................................... 433/56, 72

[56] References Cited
U.S. PATENT DOCUMENTS
2,016,103 10/1935 Chott .................................. 433/56

Primary Examiner—Robert Peshock
Attorney, Agent, or Firm—Bacon & Thomas

[57] ABSTRACT

An alignment cap for mounting artificial teeth on a working model, characterized thereby that it mainly consists of a proper arched cap made of a transparent material, e.g. a plastic, which at its back-side is hingedly fixed to an axis of rotation.

5 Claims, 7 Drawing Figures

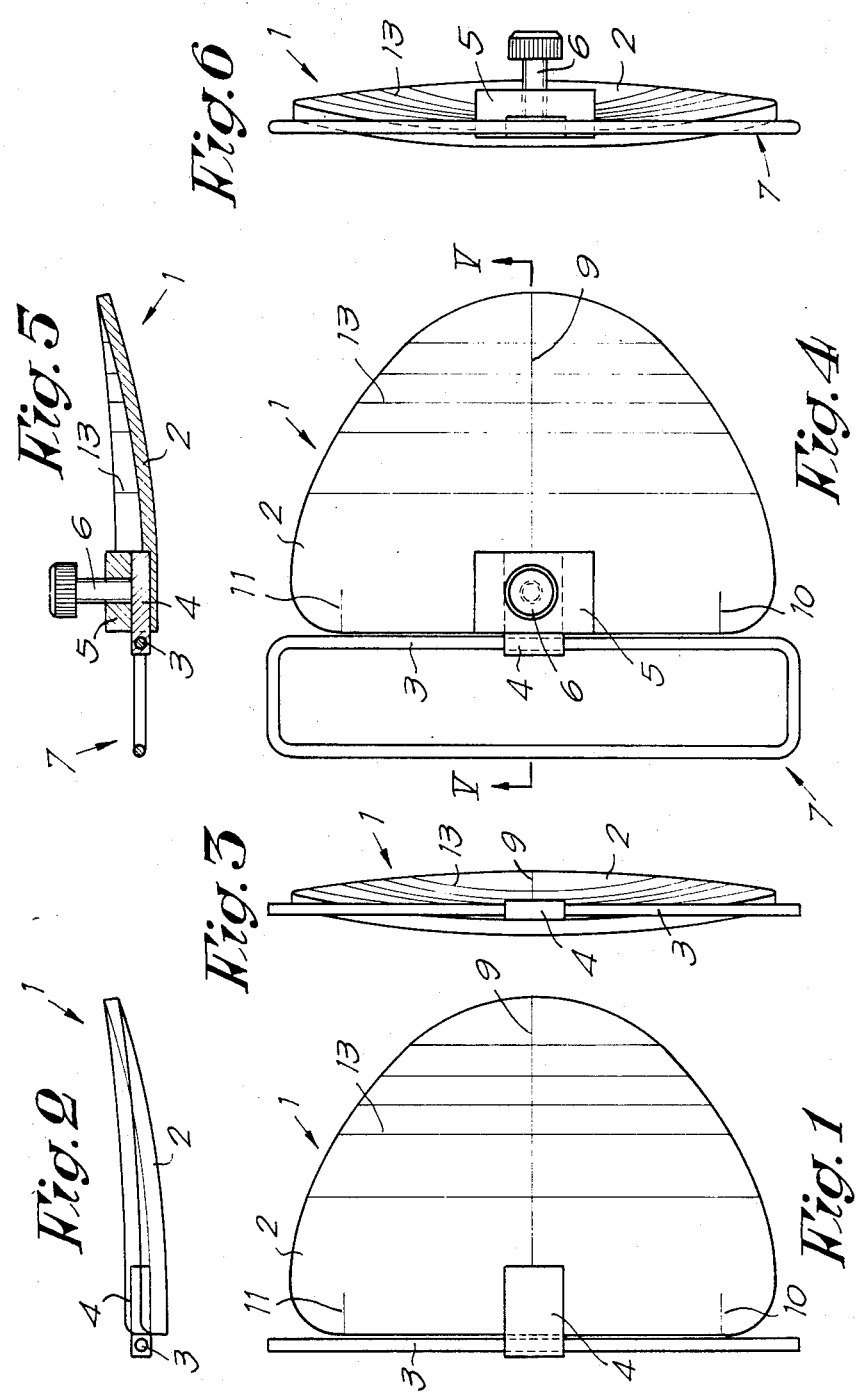

ALIGNMENT CAP FOR MOUNTING ARTIFICIAL TEETH ON WORKING MODELS

This invention relates to a so-called cap for mounting artifical teeth on a working model, especially a submaxillary model, the latter occasionally being fixed in a so-called articulator at the moment of mounting the teeth.

It results from the foregoing that the cap according to the invention is model-bound, in other words is not articulator-bound.

Up to now all known caps have been made of an opaque material and are either bound to an articulator or are loose from the articulator as well as from the model.

The main disadvantage of the known caps is that they are opaque and so hamper the visual sight on the mounted teeth and model marks.

Hence, the object of this invention is a cap for mounting artificial teeth on a submaxillary model that eliminates the above-mentioned and other disadvantages of the existing cap.

For that purpose this cap mainly consists of a proper arched cap made of a transparent material, e.g. plastic, which at its back end is hingedly fixed to an axis of rotation.

According to the invention, such a cap is placed on the submaxillary working model exclusively with respect to points of reference.

According to the invention, these points of reference are formed by the so-called retromandibular triangle, against which the axis of rotation of the cap and the cutting edge of the already mounted eye-teeth are placed.

An outstanding feature of the cap according to the invention is that it is realized in a transparent material which in addition and preferably is provided with scratched-in lines of reference.

So, it is obtained that not only the right positioning of the cap with respect to the working model can remain simple and always correctly oriented, but also that the right place and position of the artificial teeth can in advance be indicated on the cap according to anatomic points of reference of the submodel, which points are visible through the cap.

Preferably, the axis of rotation makes part of a rectangular bow which at the one hand facilitates the fixation of the cap to the working model and on the other hand, provided that the width of the bow has been determined judiciously, allows one to orient the bow and then to fix it to the model, e.g. with a kneading mass.

In order to better demonstrate the features of the invention, two preferred embodiments are described hereinafter without limiting the scope of the invention with reference to the accompanying drawings wherein:

FIG. 1 represents a top view of a cap according to the invention;

FIGS. 2 and 3 represent a side-view and a back-view respectively of the cap of FIG. 1;

FIG. 4 represents a view similar to that of FIG. 1, but for a variant of an embodiment;

FIG. 5 represents a section according to line V—V in FIG. 4;

FIG. 6 represents a back-view of the cap of FIG. 4;

Figure 7:
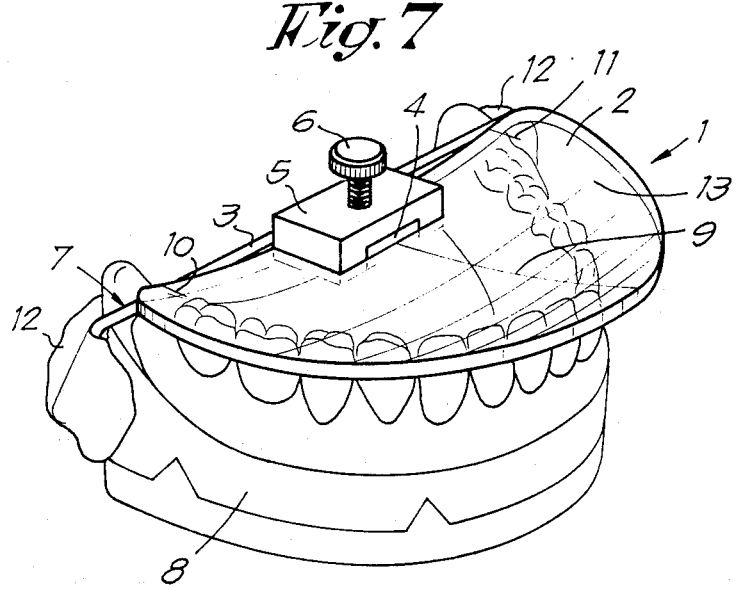
FIG. 7 represents a perspective view of a submaxillary working model provided with artificial teeth and equipped with a cap according to the invention.

In the embodiment according to FIGS. 1 to 3, said cap 1 is mainly constituted by the proper cap 2 and an axis of rotation 3 to which said cap is applied, e.g. by means of an adapter 4 wherein the axis 3 is mounted rotatably but cannot be axially displaced and that is fixed occasionally removably to the proper cap 2.

Said cap 2 is made of a transparent material, e.g. plastic, and is realized in a thickness as small as possible in order to keep optical faults as small as possible, this cap 2 exhibiting an arching.

There is nothing to prevent the realization of various caps with several archings so that the most suitable arching can be chosen for every application.

According to the invention, such a cap 2 in addition is provided with scratched-in lines in order to place such a cap in a simple way purely symmetrically to a working model on the one hand, and to facilitate the purely symmetrical mounting of artificial teeth at the other hand.

In FIGS. 5 and 6 a second embodiment is given of a cap according to the present invention which mainly differs from the first described cap in that the adapter 4 is not fixedly stuck to the proper cap 2, but can be introduced in a bridge 5 being fixedly stuck to said cap 2 and in which bridge 5 a screw 6 is provided allowing the adapter 4 to be fixed in bridge 5.

In this embodiment the axis of rotation 3 is a part of a bow or structure 7 for anchoring to the lateral side and back-side of the working model.

As appears from FIG. 7, a mounting of the teeth for a lower jaw is made by means of the transparent cap.

The axis of rotation 3 is lying against the retromandibular triangle wherein line 9 and the short lines 10–11 that are provided on the proper cap 2 were used to place said cap right in the middle of working model 8, whereupon the cap was fixed to the working model by means of adhesive material 12. The proper cap 2 can be raised or let down with respect to said working model 8 and can be adjusted and/or removed by means of the co-operating parts 4–5, the accurate replacement of the cap with respect to the working model 8 being guaranteed.

As the proper cap 2 is transparent, it is clear that mounting the artificial teeth can take place according to lines that can be applied by the dental mechanic or dentist to said proper cap 2 with a felt-tip marker or the like, whereby checking with respect to the right place can occur through said cap 2, and the parallel lines 13 likewise facilitate the purely symmetrical mounting of the artificial teeth.

It is clear that the present invention is not restricted to the embodiment described as an example and represented in the accompanying drawings; such cap according to the invention can be realized in any form and dimensions without departing from the scope of the invention.

I claim:

1. An alignment cap for mounting artificial teeth on a submaxillary working model comprising:
    (a) a cap body in the configuration of the retromandibular triangle of the working model and having a proper arch and including a backside;
    (b) the cap body being formed of transparent material for permitting viewing therethrough of teeth mounted on the working model;
    (c) anchoring means directly attachable to the lateral and back sides of the working model for defining an axis of rotation lying against the retromandibular triangle of the working model; and (d) means for connecting the backside of the cap body to the anchoring means for permitting the cap body to pivot about the axis of rotation, but not be displaceable in its axial direction, with respect to the working model.

2. The alignment cap of claim 1 further including a plurality of scratched-in lines for facilitating the symmetrical mounting of the cap to the working model and the symmetrical mounting of the teeth.

3. The alignment cap to claim 2 wherein the scratched-in lines include a plurality of lines disposed in parallel and a single line disposed perpendicular to the parallel lines and intersecting the midpoints thereof.

4. The alignment cap of claim 1 wherein the connecting means includes a bridge secured to the cap body, an adaptor pivotally connected to the anchoring means, and means for detachably connecting the adaptor to the bridge.

5. The alignment cap of claim 4 wherein the means for detachably connecting the adaptor to the bridge includes a hold-down screw.

* * * * *